United States Patent
Wu et al.

(10) Patent No.: US 11,883,982 B2
(45) Date of Patent: *Jan. 30, 2024

(54) METHOD FOR COMPRESSION CASTING CONCRETE TO REDUCE CEMENT

(71) Applicant: SHENZHEN UNIVERSITY, Guangdong (CN)

(72) Inventors: Yufei Wu, Guangdong (CN); Biao Hu, Guangdong (CN); Xun Wang, Guangdong (CN)

(73) Assignee: Shenzhen University, Guangdong (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/127,522

(22) Filed: Mar. 28, 2023

(65) Prior Publication Data
US 2023/0321868 A1  Oct. 12, 2023

(30) Foreign Application Priority Data
Apr. 7, 2022  (CN) .......................... 202210360079.3

(51) Int. Cl.
   *B28B 3/02*    (2006.01)
   *B28B 17/00*   (2006.01)
   (Continued)

(52) U.S. Cl.
   CPC .............. *B28C 5/003* (2013.01); *B28B 3/022* (2013.01); *B28B 17/0081* (2013.01);
   (Continued)

(58) Field of Classification Search
   CPC ......... B32B 3/022; B28C 5/003; B28C 5/386; B28C 5/402; C04B 2111/00051;
   (Continued)

(56) References Cited

U.S. PATENT DOCUMENTS 3,917,781 A * 11/1975 Gabriel ............... B28B 23/0081
                                              264/333
3,927,163 A * 12/1975 Gabriel ................... B28B 7/465
                                              264/333

FOREIGN PATENT DOCUMENTS

CN   108501183 A  *  9/2018  ............. B28B 11/04
CN   113378400 A  *  9/2021
CN   113910447 A  *  1/2022

OTHER PUBLICATIONS

"Reducing Cement Content in Concrete Mixtures"; NPL, Wisconsin Highway Research Program (Dec. 2011) (Year: 2011).*

(Continued)

*Primary Examiner* — Francisco W Tschen
*Assistant Examiner* — Edgaredmanuel Troche
(74) *Attorney, Agent, or Firm* — Neugeboren O'Dowd PC

(57) ABSTRACT

The present disclosure discloses a method for compression casting concrete to reduce the amount of cement, including: adopting any existing concrete mix proportion designed for concrete of given strength, mixing the concrete, pouring the concrete into a mould, and compressing the concrete at a given pressure, where 28-day strength of the compacted concrete is increased; gradually reducing the amount of cement while keeping the amounts of other materials unchanged, where 28-day strength of the concrete is gradually reduced until the concrete meets a design index; proportionally reducing amounts of water and cement in a last mix proportion while keeping the amounts of other materials unchanged, where during compression casting of the concrete, discharge of cement paste is gradually reduced until no cement paste is discharged; and compression casting a concrete member according to a final mix proportion.

10 Claims, 2 Drawing Sheets

(51) Int. Cl.
  *C04B 40/00* (2006.01)
  *B28C 5/00* (2006.01)
  *C04B 111/00* (2006.01)
(52) U.S. Cl.
  CPC . *C04B 40/0096* (2013.01); *C04B 2111/00051* (2013.01); *C04B 2111/00068* (2013.01)
(58) Field of Classification Search
  CPC . C04B 2111/00068; C04B 2111/00017; C04B 2111/00034; C04B 2111/00077; C04B 2111/10; C04B 7/13; Y10T 29/4976
  USPC ........ 264/71, 228, 297.9, 664, 69, 232, 239, 264/299, 334, 336
  See application file for complete search history.

(56) References Cited

OTHER PUBLICATIONS

"Improving Concrete through Reduced Cement Factors"; NPL, US Department of Transportation, Federal Highway Administration; (Apr. 20, 2017) (Year: 2017).*

"Concrete Mixture Optimization Using Statistical Methods"; NPL, US Department of Transportation, Federal Highway Administration , Publication No. FHWA-RD-03-060 (Apr. 11, 2004) (Year: 2004).*

Taylor et al., "Optimum material ratio for improving the performance of cement-mixed soils"; (2021); Transportation Geotechnics 28 (2021) 100544 (Year: 2021).*

ASTM Designation: C192/C192M-14; "Standard Practice for Making and Curing Concrete Test Specimens in the Laboratory" (Year: 2023).*

CNIPA, "Notification to Grant Patent Rights for Invention for Chinese Patent Application No. 202210360079.3," p. 3; Published in: CN.

CNIPA, "Office Action Issued in Chinese Patent Application No. 202210360079.3", dated Aug. 10, 2022, p. 10, Published in: CN.

CNIPA, "CN Grant Text CN114714478A for Chinese Patent Application No. 202210360079 .3", dated Jul. 8, 2022, p. 12, Published in: CN.

Wu, Yu-Fei et al., "Effect of compression casting method on the compressive strength, elastic modulus and microstructure of rubber concrete," Journal of Cleaner Production, 264, (2020) 121746, p. 13, Published in: US.

Qianyan, "Sand for Construction," GB/T, 14684-2011, p. 34, Published in: CN.

Qianyan, "pebble and crushed stone for construction," GB/T, 14685-2011, p. 33, Published in: CN.

Qianyan, "Standard for Test Methods of Physical and Mechanical Properties of Concrete," GBT 50081-2019, p. 113, Published in: CN.

* cited by examiner

METHOD FOR COMPRESSION CASTING CONCRETE TO REDUCE CEMENT

CROSS REFERENCE TO RELATED APPLICATION

This patent application claims the benefit and priority of Chinese Patent Application No. 202210360079.3, filed with the China National Intellectual Property Administration on Apr. 7, 2022, the disclosure of which is incorporated by reference herein in its entirety as part of the present application.

TECHNICAL FIELD

The present disclosure relates to the technical field of concrete casting, and in particular, to a method for compression casting concrete to reduce the amount of cement.

BACKGROUND

According to statistics, the production of every one kg of ordinary Portland cement causes 0.75-0.9 kg of carbon dioxide emission. Cement is cost-ineffective since the consumption of concrete is huge. Therefore, it can be known that the mass use of cement imposes a great burden on carbon dioxide emissions and the cost of construction management. To promote the development of the construction industry from high energy consumption and high carbon emissions to the green, low-carbon and economical direction, it is necessary to reduce the amount of cement as much as possible while ensuring the quality of concrete.

Commonly, there are two ways to reduce the amount of cement in traditional concrete technology.

The first method is to use a cement alternative. That is, during the preparation of the concrete, cement is replaced with additional materials such as fly ash, grated blast furnace slag, calcined clay, unburned and ground limestone or recycled concrete fine particles without affecting the working performance of concrete, to reduce the amount of cement. However, this method usually has some disadvantages, such as a low substitution rate, the influence on concrete performance, special requirements for the service environment, and not obvious economic advantages of substitutes.

The second is the optimization design method. That is, a novel type of cement with low carbon emissions is designed for the cement production process. In the process of concrete production, the optimal concrete mix proportion and aggregate grading are designed to reduce the amount of traditional cement with high carbon emissions. However, at present, there cement that can compete with ordinary Portland cement in terms of economy and effectiveness is lacking, or limited to laboratory trial stages and far from commercial scale.

Therefore, the prior art needs to be improved.

SUMMARY

In view of the shortcomings of the prior art, an objective of the present disclosure is to provide a method for compression casting concrete by reducing an amount of cement, aiming to reduce an amount of cement in existing concrete mixtures.

To achieve the above objective, the present disclosure adopts the following technical solutions.

In a first aspect, the embodiment of the present disclosure provides a method for compression casting concrete to reduce the amount of cement, including the following steps:

mixing concrete raw materials according to any existing concrete mix proportion designed to meet a specific performance requirement;

pouring mixed fresh concrete into a mould, and compressing the concrete in the mould using a compression device at a set pressure, such that the concrete is compacted and excess cement paste is extruded;

gradually reducing the amount of cement in the concrete mix proportion while keeping amounts of other materials unchanged since the performance of the compression cast concrete exceeds the original performance index of normal cast concrete. Each reduction in the amount of cement gives a new concrete mix. The strength of the compression cast new concrete mix after 28-day of curing is gradually reduced until the performance of the new concrete is reduced to meet a design index;

proportionally reducing amounts of water and cement in the last mix proportion obtained in the previous step while keeping amounts of other materials unchanged. A new concrete mix is obtained each time the amounts of water and cement in the mix proportion are reduced, where during compression casting of the new concrete mix, discharge of cement paste is gradually reduced until there is no cement paste, or only a small amount of cement paste is discharged after the compression casting. At this time, the amount of cement is a minimum amount of cement in the mix of the compression cast concrete meeting a performance index, and this mix proportion is used as a final mix proportion of the compression cast concrete; and compression casting concrete member according to the final mix proportion.

As a further improved technical solution, the method for compression casting concrete to reduce the amount of cement includes the following steps before the step of mixing concrete raw materials according to any existing concrete mix proportion designed for specific concrete performance requirements: selecting and preparing the concrete raw materials required for concrete preparation.

As a further improved technical solution, in the method for compression casting concrete to reduce the amount of cement, the concrete raw materials include water, cement, coarse aggregates, and fine aggregates.

As a further improved technical solution, the method for compression casting concrete to reduce the amount of cement further includes the following steps after the step of pouring concrete into a mould:

vibrating the concrete in the mould with an insert-type vibrator to make the vibrated concrete reach a preset height in the mould; and aligning and leveling the mould and the compression device.

As a further improved technical solution, the method for compression casting concrete to reduce the amount of cement further includes the following step before the step of compressing the concrete in the mould using a compression device at a set pressure: setting compression parameters.

As a further improved technical solution, in the method for compression casting concrete to reduce the amount of cement, the compression parameters include the set pressure and compression time.

As a further improved technical solution, in the method for compression casting concrete to reduce the amount of cement, a process of gradually reducing the amount of cement in the concrete mix proportion while keeping amounts of other materials unchanged specifically includes:

reducing the amount of cement in the initially given mix proportion while keeping the amounts of water, coarse aggregates, and fine aggregates unchanged.

As a further improved technical solution, in the method for compression casting concrete to reduce the amount of cement, a process of proportionally reducing amounts of water and cement in a last mix proportion while keeping amounts of other materials unchanged specifically includes:

proportionally reducing the amounts of cement and water in the mix proportion while keeping the amounts of coarse aggregates and fine aggregates unchanged.

As a further improved technical solution, in the method for compression casting concrete to reduce the amount of cement, the set pressure is larger than or equal to 5 MPa.

As a further improved technical solution, in the method for compression casting concrete to reduce the amount of cement, the compression time is greater than 2 minutes.

The technical solution adopted in the present disclosure has the following beneficial effects:

The method for compression casting concrete to reduce the amount of cement provided by the present disclosure includes the following steps: mixing concrete raw materials according to any existing concrete mix proportion designed for specific concrete performance requirement; pouring obtained mixed fresh concrete into a mould, and compressing the concrete in the mould using a compression device at a set pressure, such that the concrete is compacted and excess cement slurry is extruded; gradually reducing the amount of cement in the concrete mix proportion while keeping amounts of other materials unchanged since the performance of the compression cast concrete exceeds the original performance index of normal cast concrete, and obtaining a new mix proportion each time the amount of cement is reduced, where the 28-day strength of compression cast concrete obtained at the new mix proportion is gradually reduced until performance of the concrete is reduced to meet a design index; proportionally reducing amounts of water and cement in a last mix ratio while keeping amounts of other materials unchanged, and compression casting concrete of a new formula obtained each time the amounts of water and cement in the mix proportion are reduced, where during compression of the concrete of the new formula, discharge of cement paste is gradually reduced until there is no cement slurry, or only a small amount of cement paste is discharged after the compression; and at this time, the amount of cement is a minimum amount of cement in formulas of the compression cast concrete meeting a performance index, and a mix proportion is used as a final mix proportion of the compression cast concrete; and compression casting a concrete member according to the final mix proportion. The method compacts the concrete during the compression, and reduces the amount of cement in the concrete, so as to achieve cost-effectiveness of concrete materials and ensure that the compressive strength of the concrete is not reduced, and the elastic modulus and durability are improved while reducing the amount of cement.

DETAILED DESCRIPTION OF THE EMBODIMENTS

Figure 1:
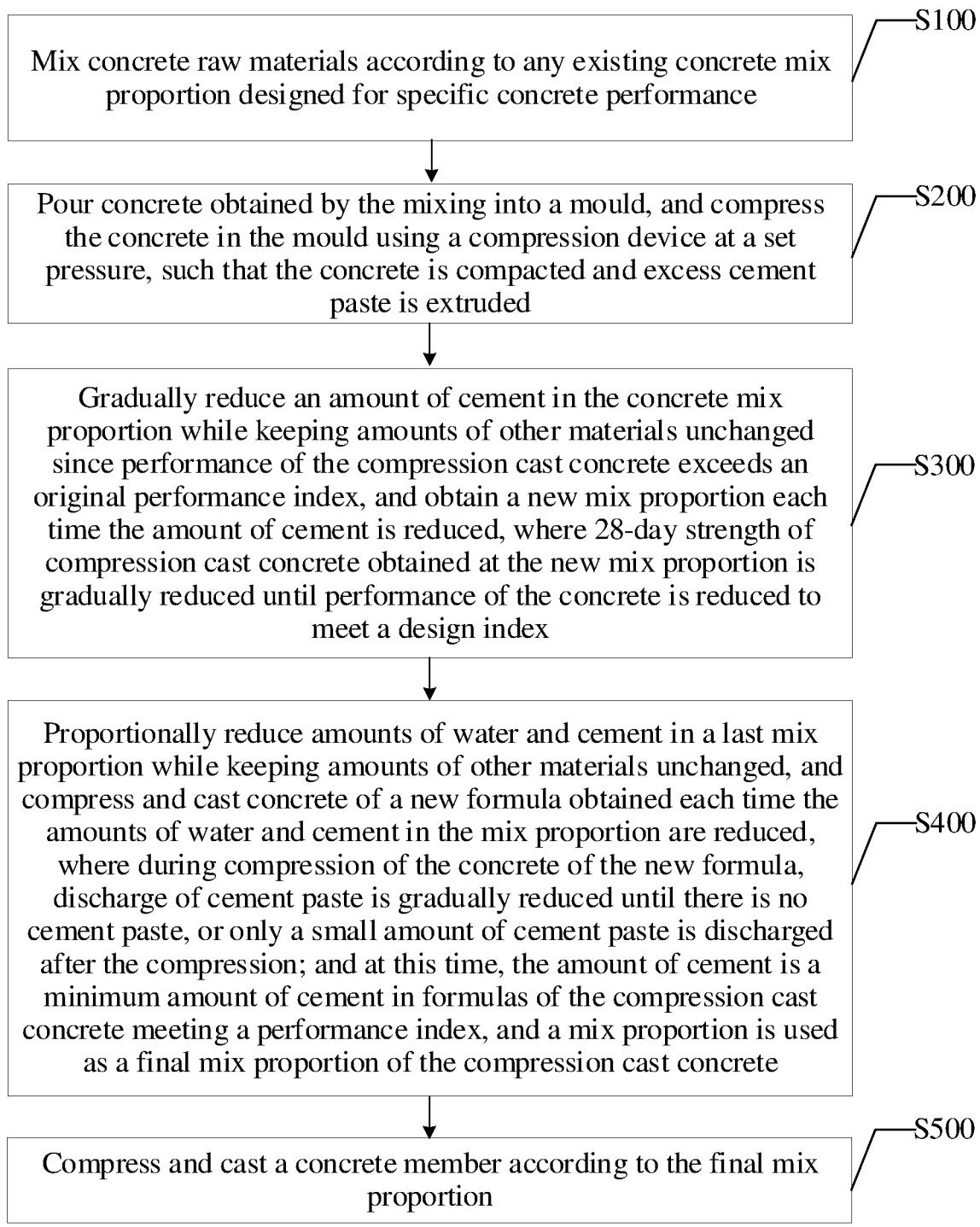
FIG. 1 is a flow chart of a preferred embodiment of a method for compression casting concrete to reduce the amount of cement provided by the present disclosure.

To facilitate the understanding of the present disclosure, the present disclosure will be described more completely below with reference to the related accompanying drawings. The preferred embodiments of the present disclosure are shown in the drawings. However, the present disclosure may be embodied in various forms without being limited to the embodiments described herein. On the contrary, these embodiments are provided to make the present disclosure more thorough and comprehensive.

Unless otherwise defined, all technical and scientific terms used herein have the same meaning as commonly understood by those skilled in the technical field of the present disclosure. The terms used herein in the specification of the present disclosure are merely for the purpose of describing specific embodiments and are not intended to limit the present disclosure.

In the embodiments and the scope of patent applications, "one" and "the" can generally refer to one or more unless specifically defined herein.

Moreover, the terms such as "first", "second", and the like described in the embodiments of the present disclosure are used herein only for the purpose of description and are not intended to indicate or imply relative importance, or implicitly indicate the number of the indicated technical features. Thus, features limited by "first" and "second" may expressly or implicitly include at least one of these features. Further, the technical solutions of the embodiments may be combined with each other on the basis that the combination is implementable by those of ordinary skill in the art. In case a combination of the technical solutions is contradictory or infeasible, such a combination is deemed inexistent and not falling within the protection scope of the present disclosure.

The commonly used methods to reduce the amount of cement in traditional concrete technology include replacing cement with additional materials such as fly ash or optimizing the design in the cement production process. The method of replacing cement with additional materials usually has some disadvantages, such as a low substitution rate, the influence on concrete performance, special requirements for the service environment, and non obvious economic advantages of substitutes. However, cement that can compete with ordinary Portland cement in terms of economy and effectiveness is lacking, or limited to laboratory trial stages and far from commercial scale.

Based on this, the present disclosure hopes to provide a solution to the above technical problems, the details of which will be elaborated on in the subsequent embodiments.

Referring to FIG. 1, FIG. 1 is a flow chart of a preferred embodiment of a method for compression casting concrete to reduce the amount of cement provided by the present disclosure. Before the embodiment of the present disclosure, the method includes the following steps.

S100, Concrete raw materials are mixed according to any existing concrete mix proportion designed for specific concrete performance requirements.

Specifically, the concrete raw materials include water, cement, coarse aggregates (such as stone), and fine aggregates (such as sand). In other embodiments, the concrete raw materials selected by the present disclosure may also be materials that can be used to prepare concrete such as recycled orthopedic materials, rubber particles, seawater and sea sand materials, and fiber materials, and are not limited to water, cement, coarse aggregates, and fine aggregates. Any existing concrete mix ratio designed for a specific concrete performance requirement is defined as the initially given mix proportion. The initial mix proportion can be selected according to the performance indexes of concrete, or according to the design standards within the industry. Optionally, the performance indexes include design strength, water permeability, and durability. After the mixing is completed, the concrete raw materials are mixed evenly. During the concrete mixing, the commonly used concrete mixer can be selected to mix the concrete raw materials into fresh concrete.

S200, Obtained mixed fresh concrete is poured into a mould, and the concrete in the mould is compressed using a compression device at a set pressure, such that the concrete is compacted and excess cement paste is extruded.

Specifically, the mixed fresh concrete is poured into the mould, which is then compressed using the compression device at the set pressure (generally greater than 5 MPa) to extrude excess cement slurry in the process of compacting the concrete. The mixed concrete needs to be poured into the mould for setting. The compression device provided by the present disclosure can compress the concrete in the mould to reduce the porosity of the concrete and extrude excess water and cement paste. As a result, the amount of cement in the concrete is reduced and the compressive strength is enhanced. It should be noted that the present disclosure does not limit the shape of the mould, and common ones such as cylindrical mould, square mould and prismatic mould can be used. The specific shape of the mould should depend on the actual use. The compression device is configured to compress the concrete in the mould. Therefore, the shape of the compression device is not limited. Under any mould shape and compression casting conditions (pressure and compression time), the mixed concrete is added to the mould, and immediately pressurized to a set pressure (e.g., 5-15 MPa) to compact the concrete. After the compression is maintained for a certain amount of time (generally greater than two minutes for ordinary concrete, and for aggregates with large elasticity, such as rubber concrete, the volume needs to be kept unchanged until the initial setting), the mould can be immediately removed.

S300, The amount of cement in the concrete mix proportion is gradually reduced while keeping amounts of other materials unchanged since the performance of the compression-cast concrete exceeds the original performance index, and a new mix proportion is obtained each time the amount of cement is reduced. The 28-day strength of compression cast concrete obtained at the new mix proportion is gradually reduced until the performance of the concrete is reduced to meet a design index.

Specifically, because the concrete becomes compact after compression casting, its actual performance index exceeds the original performance index. For example, the actual strength of concrete at this time has far exceeded the designed target strength, which means that the content of cement in concrete at this time is too much. At this time, the amount of cement in the concrete mix proportion can be continuously reduced proportionally (the amounts of other materials remains unchanged). A new mix proportion is obtained each time the amount of cement is reduced. The compression cast concrete obtained at each new mix proportion needs to be de-moulded and cured for 28 days, and the axial compression test is carried out to evaluate the relationship between cement reduction and strength. In other words, the 28-day strength of compression-cast concrete obtained at the new mix proportion is gradually reduced until the performance of the compression-cast concrete just meets or slightly exceeds the required performance index (this is the first level of reducing the amount of cement).

S400, Amounts of water and cement in the last mix proportion obtained in the previous step are proportionally reduced while keeping amounts of other materials unchanged, and a new concrete mix is obtained each time the amounts of water and cement in the mix proportion are reduced. During compression of the new concrete mix, the discharge of cement paste is gradually reduced until there is no cement paste, or only a small amount of cement paste is discharged after the compression. At this time, the amount of cement is the minimum amount of cement in the concrete mix of the compression cast concrete meeting a certain performance index, and this mix proportion is used as the final mix proportion of the compression cast concrete.

It can be understood that when the discharge of cement paste is observed, if no cement paste flows out of the mould, or only a small amount of cement paste flows out, the amount of cement is minimized. Therefore, the compressed concrete achieves the effect of a low amount of cement and high strength, and the mix proportion with the minimum amount of cement can be determined as the final mix proportion of compression cast concrete. Since the performance of the compression cast concrete has met the performance index, based on which this step is mainly to minimize the amount of cement, that is, to minimize the amount of cement based on meeting the design performance of concrete, taking into account practicability and economical efficiency.

S500, A concrete member is compressed and cast according to the final mix proportion.

Specifically, according to the final mix proportion, the concrete raw materials are mixed. The mixed concrete is then poured into the mould, and the concrete in the mould is compressed using the compression device at the set pressure. The compressed concrete is de-moulded and cured to obtain the concrete member.

After the concrete member is obtained, it is verified whether it meets the performance indexes such as design strength, water permeability, and durability. If the design index is exceeded, the amount of cement can be further reduced. If it is lower than the design target, the amount of cement can be increased. The above processes are repeated until the indexes are just met.

The method for compression casting concrete to reduce the amount of cement provided in the embodiment of the present disclosure can reduce the amount of cement, improve the compressive strength of concrete, reduce the porosity, and improve the durability of concrete. Compared with the method of using alternative materials to partially replace cement, the embodiment of the present disclosure does not need to add mineral admixtures and chemical admixtures but uses the physical compression method to improve the strength of concrete while reducing the amount of cement. Compared with the concrete mix optimization design method, the embodiment of the present disclosure can reduce the amount of cement while improving the strength or keeping the strength from decreasing for any mix proportion of concrete. The method applies to any kind of concrete, including ordinary concrete, recycled concrete, rubber concrete, etc., which has strong applicability, simple operation, and a unified process. The embodiment of the present disclosure applies to any shape (cylinder, prism, cube, etc.) of the precast concrete member, including concrete block, beam, plate, column, etc.

Exemplarily, the method includes the following step before the step of mixing concrete raw materials according to any existing concrete mix proportion designed for specific concrete performance index requirements.

S10, The concrete raw materials required for concrete preparation are selected and prepared.

Specifically, referring to FIG. 1, before the step of mixing concrete raw materials according to any existing concrete mix proportion designed for a specific concrete performance index, the present disclosure selects and prepares the concrete raw materials required. In other embodiments of the present disclosure, for the selection and preparation of the concrete raw materials required for concrete preparation, selection may be specifically performed according to specific concrete use scenarios. For example, the coarse and fine aggregates required by concrete can be selected and prepared according to "Standard for test methods of concrete physical and mechanical properties" GB/T 50081-2019, "Pebble and crushed stone for construction" GB/T 14685-2011, and "Sand for construction" GB/T 14684-2011, so as to determine the initially given mix proportion of concrete, and then mix the concrete.

Exemplarily, the method further includes the following steps after the step of pouring the mixed concrete into a mould.

S210, The concrete in the mould is vibrated with an insert-type vibrator to make the vibrated concrete reach a preset height in the mould.

S220, The mould and the compression device are aligned and leveled.

It can be understood that after the mixed concrete is poured into the mould, bubbles shall be excluded from the concrete. The use of the insert-type vibrator for vibration can make the concrete tightly combined, and eliminate the honeycomb and pitted surface of the concrete, so as to improve its strength and ensure the quality of the concrete member. The vibrator is a kind of machine used in engineering construction, which can make the concrete tightly combined, eliminate the honeycomb and pitted surface of the concrete, and improve the strength. Vibrators are classified according to the method of vibration transmission, power source, and vibration frequency. After vibration, the concrete can reach the preset height in the mould. Further, the mould and the compression device are aligned and leveled. It can balance the concrete in the mould, and facilitate the alignment of the mould and the compression device. Then the compression device can apply pressure to the concrete in the mould. If the alignment is not accurate, it is easy to make the compression device deflect or bend during the compression of concrete. Therefore, more accurate leveling and alignment indicate stronger protection of instruments and equipment, and the service life of instruments and equipment can be improved.

Further, the method further includes the following step before the step of compressing the concrete in the mould using a compression device at a set pressure.

S230, Setting the compression parameters, including the set of pressure, compression time, and the shape of the mould.

It can be understood that when the pressure reaches a certain value, a greater pressure indicates a higher concrete strength. Therefore, the compression parameters are set and adjusted, including the pressure and the compression time. In this way, the concrete strength can be maximized. Optionally, the pressure is greater than or equal to 5 MPa, and the compression time is generally greater than two minutes. Of course, different concrete materials need different compression parameters. For example, for ordinary concrete, the compression time is generally greater than two minutes. For aggregates with large elasticity, such as rubber concrete, the volume needs to be kept unchanged, and the mould is removed immediately after the initial setting of compressed concrete. In the specific embodiment, for the current cylinder mould with a diameter of 150 mm and a height of 300 mm, it can be seen from the test results of compression casting concrete that when the pressure is less than 15 MPa, a greater pressure indicates a higher concrete strength. However, when the pressure is greater than 15 MPa, the increment of concrete strength decreases. In addition, different compression times exerted little effect on the strength improvement of concrete.

Exemplarily, a process of gradually reducing the amount of cement in the concrete mix proportion while keeping amounts of other materials unchanged specifically includes the following sub-step.

S310, The amount of cement in the initially given mix proportion is reduced while keeping the amounts of water, coarse aggregates, and fine aggregates unchanged.

It can be understood that in the process of compression in this step, the performance of concrete does not exceed the original performance index mainly to reduce the amount of cement. Therefore, a new mix proportion is obtained each time the amount of cement is reduced. The 28-day strength of compression cast concrete obtained at the new mix proportion is gradually reduced until the performance of the concrete is reduced to meet a certain design index.

Exemplarily, a process of proportionally reducing amounts of water and cement in the last mix proportion while keeping amounts of other materials unchanged specifically includes the following sub-step.

S410, The amounts of cement and water in the mix proportion are reduced proportionally while keeping the amounts of coarse aggregates and fine aggregates unchanged.

It can be understood that the performance has been reduced to meet the design index. Therefore, in the process of compression in this step, the amounts of water and cement are reduced proportionally, such that the minimum amount of cement of the compression cast concrete can be achieved under the condition of meeting the performance index.

The following is a detailed description of the method for compression casting concrete to reduce the amount of cement provided by the present disclosure in combination with the specific application scenarios.

In the embodiment of the present disclosure, the concrete mix proportion of C30 and C60 (with cylinder strength of 25 MPa and 50 MPa, respectively) are designed for comparison. The coarse and fine aggregates with certain aggregate grading are selected, and the physical and mechanical performance indexes of the coarse aggregates are tested. Under the optimized compression casting technology conditions (i.e. pressurization of 15 MPa for two minutes while keeping the pressure unchanged), compression casting treatment is performed on both ordinary C30 concrete and C30 concrete with proportionally reduced water and cement (notably, the amounts of the coarse aggregates and the fine aggregates kept unchanged). The relationship between cement reduction and compressive strength is evaluated through the compressive test of the concrete specimens after 28 days of curing. Finally, an economical and environment-friendly compression cast concrete member with a low amount of cement, high compressive strength and low porosity is obtained.

Table 1, Table 2 and Table 3 summarize some details of the compression tests of standard concrete cylinders (150 mm in diameter and 300 mm in height) conducted in the present disclosure, including the physical and mechanical properties of aggregates, the mix proportion of ordinary concrete, the mix proportion of compression cast concrete with different cement contents, and the number of specimens.

TABLE 1

Properties of aggregate

| Type | Apparent density (kg/m$^3$) | Water absorption (%) | Crushing indicator (%) |
|---|---|---|---|
| Coarse aggregates (stone) | 2650 | 1.2 | 16.9 |

TABLE 2

Mix proportion of ordinary concrete

| Mix | Coarse aggregate (kg/m$^3$) | Water (kg/m$^3$) | Cement (kg/m$^3$) | Sand (kg/m$^3$) |
|---|---|---|---|---|
| C30 | 1128 | 201 | 380 | 691 |
| C60 | 958 | 213 | 575 | 610 |

Note: The cement used in this patent application is ordinary Portland cement, grade 42.5.

TABLE 3

Mix proportion of ordinary concrete and compression cast concrete with different amounts of cement

| Specimen No. | Coarse aggregate (kg/m$^3$) | Water (kg/m$^3$) | Cement (kg/m$^3$) | Sand (kg/m$^3$) | W/C | Ordinary concrete specimen (pieces) | 28-day cylinder strength (MPa) | Compressed concrete specimen (pieces) | 28-day cylinder strength (MPa) |
|---|---|---|---|---|---|---|---|---|---|
| 1 | 1128 | 201 | 380 | 691 | 0.53 | 3 | 26.90<br>29.41<br>27.31 | 3 | 50.07<br>49.48<br>49.40 |
| 2 | 1128 | 168.01 | 317 | 691 | 0.53 | 3 | 31.12<br>28.48<br>30.21 | 3 | 50.46<br>53.33<br>50.05 |
| 3 | 958 | 213 | 575 | 610 | 0.37 | 3 | 49.4<br>50.5<br>50.9 | | |

Figure 2:
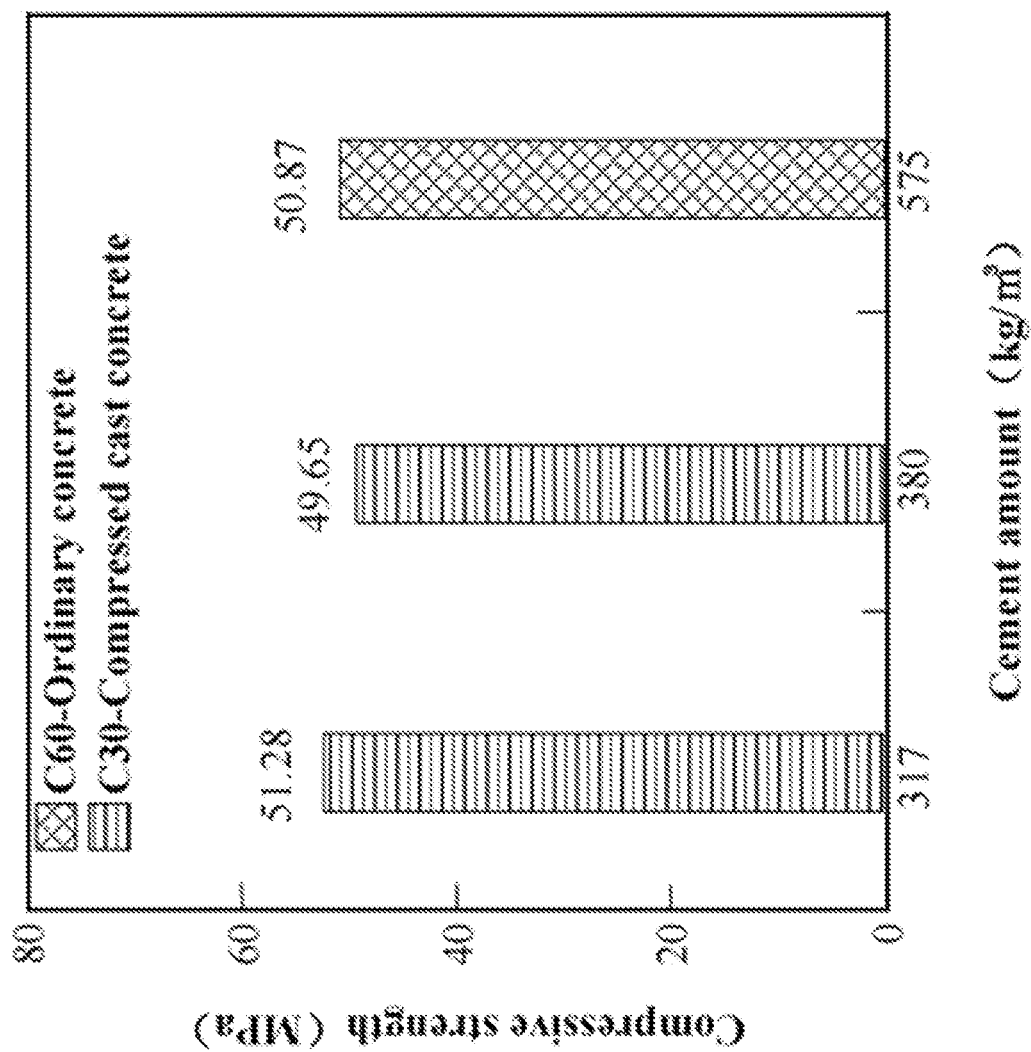
FIG. 2 is a comparison diagram of the average strength of concrete specimens with different mix proportions in the present disclosure.

FIG. 2 shows the average compressive strength of ordinary concrete and compression cast concrete cured for 28 days with different mix proportions. By comparing the strength of compression-cast concrete C30 and ordinary concrete C60 without compression casting in FIG. 2, under the condition that mineral admixtures and chemical admixtures are not allowed to use, it is necessary to optimize the mix proportion of ordinary concrete and reduce the amounts of water and cement when the strength of ordinary concrete is required to reach 50 MPa. When the amount of cement in the mix is 575 kg/m$^3$, the compressive strength close to 50 MPa can be obtained. However, using the compression casting method in the present disclosure, the average strength of ordinary concrete C30 (specimen 2 in Table 3) with a cement content of only 317 kg/m$^3$ reaches 51.3 MPa after compression casting, effectively reducing the amount of cement by about 45%.

In the process of concrete compression casting, a large amount of cement slurry is discharged, and this wasted cement paste can be further saved. Thus, when the water-to-cement ratio (W/C) is constant, the amounts of cement and water can be further reduced proportionally, until no or very little cement slurry is discharged from the mould. For example, the compression-cast concrete with an amount of cement of 380 kg/m$^3$ (specimen 1 in Table 3) still has cement slurry outflow during compression, and the average strength at this time is 49.7 MPa. When the cement content is further reduced to 317 kg/m$^3$, there is almost no cement paste outflow during compression casting, and the average strength is 51.3 MPa. At this time, the amount of cement in the mix proportion of compression cast concrete is the lowest.

In conclusion, the present disclosure provides the method for compressing and casting concrete to reduce the amount of cement, including the following steps. Any existing concrete mix proportion designed for concrete of given strength is adopted. The concrete is mixed and poured into a mould, which is then compressed at a given pressure. The 28-day strength of the compacted concrete is increased and beyond the original one. Thus, the amount of cement can be gradually reduced while keeping the amounts of other materials unchanged. The 28-day strength of the concrete with reduced cement content is gradually decreased until the concrete meets the design index. Then, the amounts of water and cement in the last mix proportion are proportionally reduced while keeping amounts of other materials unchanged. Thus, during compression casting of the concrete, the discharge of cement paste is gradually reduced until no cement paste is discharged. Concrete members are made using the compression cast method according to the final concrete mix proportion. The method compacts the concrete by compression casting, reduces the amount of cement in the concrete, and ensures that the performance of the compression-cast concrete is not lower than that of the normal cast concrete using the original mix proportion, thus reducing the cost of concrete materials.

Those skilled in the art may easily think of other implementation solutions for the present disclosure after considering the specification and practicing the content disclosed herein. The present disclosure is intended to cover any variations, uses, or adaptive changes of the present disclosure. These variations, uses, or adaptive changes follow the general principles of the present disclosure and include common knowledge or conventional technical means in the technical field that are not disclosed by the present disclosure. The specification and the embodiments are to be regarded as examples only, and the true scope and spirit of the present disclosure are pointed out by the claims.

What is claimed is:

1. A method for compression casting concrete to reduce an amount of cement, comprising the following steps:
    mixing concrete raw materials according to any existing concrete mix proportion designed to meet a specific performance requirement, the concrete mix proportion comprising at least water and a cement;
    pouring the concrete obtained by the mixing into a mould, and compressing the concrete in the mould using a compression device at a set pressure, such that the concrete is compacted and excess cement paste is extruded;
    gradually reducing the amount of the cement in the concrete mix proportion while keeping amounts of other materials unchanged since the performance of the compression cast concrete exceeds an original performance index, and obtaining a new mix proportion each time the amount of the cement is reduced; and demoulding the compression cast concrete obtained at each new mix proportion and curing for 28 days, and carrying out a compressive strength axial compression test to evaluate a relationship between cement reduction and strength, wherein the 28-day strength of the compression cast concrete obtained at the new mix proportion is gradually reduced until the performance of the concrete is reduced to meet a design index, and a mix proportion at this time is obtained as a mediate mix proportion;
    proportionally reducing amounts of the water and the cement in the mediate mix proportion while keeping amounts of other materials unchanged, and compressing and casting concrete of a new formula obtained each time the amounts of water and cement in the mediate mix proportion are reduced proportionally, wherein during compression of the concrete of the new formula, discharge of cement paste is gradually reduced until there is no cement slurry discharged after the compression; and at this time, the amount of cement is a minimum amount of cement in formulas of the compression cast concrete meeting a performance index, and the mix proportion is used as a final mix proportion of the compression cast concrete; and
    compression casting a concrete member according to the final mix proportion.

2. The method for compression casting concrete to reduce the amount of cement according to claim 1, comprising the following step before the step of mixing concrete raw materials according to any existing concrete mix proportion designed for specific concrete performance:
    selecting and preparing the concrete raw materials required for concrete preparation.

3. The method for compression casting concrete to reduce the amount of cement according to claim 1, wherein the concrete raw materials comprise, but are not limited to, the water, the cement, coarse aggregates, and fine aggregates.

4. The method for compression casting concrete to reduce the amount of cement according to claim 3, wherein a process of gradually reducing the amount of the cement in the concrete mix proportion while keeping amounts of other materials unchanged specifically comprises:
    reducing the amount of the cement in the initially given mix proportion while keeping the amounts of water, coarse aggregates, and fine aggregates unchanged.

5. The method for compression casting concrete to reduce the amount of cement according to claim 4, wherein a process of proportionally reducing amounts of water and cement in the mediate mix proportion while keeping amounts of other materials unchanged specifically comprises:
    proportionally reducing the amounts of the cement and the water in the mediate mix proportion while keeping the amounts of the coarse aggregates and the fine aggregates unchanged.

6. The method for compression casting concrete to reduce the amount of cement according to claim 1, further comprising the following steps after the step of pouring the concrete obtained by the mixing into the mould:
    vibrating the concrete in the mould with an insert-type vibrator to make the vibrated concrete reach a preset height in the mould; and
    aligning and leveling the mould and the compression device.

7. The method for compression casting concrete to reduce the amount of cement according to claim 6, further comprising the following step before the step of compressing the concrete in the mould using a compression device at a set pressure: setting compression parameters.

8. The method for compression casting concrete to reduce the amount of cement according to claim 7, wherein the compression parameters comprise the set pressure and compression time.

9. The method for compression casting concrete to reduce the amount of cement according to claim 8, wherein the set pressure is greater than or equal to 5 MPa.

10. The method for compression casting concrete to reduce the amount of cement according to claim 8, wherein the compression time is greater than 2 minutes.

* * * * *